(12) United States Patent
Butler et al.

(10) Patent No.: US 8,182,518 B2
(45) Date of Patent: May 22, 2012

(54) STATIC AND DYNAMIC CERVICAL PLATES AND CERVICAL PLATE CONSTRUCTS

(75) Inventors: Michael S. Butler, Fishers, IN (US); Jeffrey C. Wang, Sherman Oaks, CA (US)

(73) Assignee: Life Spine, Inc., Hoffman Estates, IL (US)

( * ) Notice: Subject to any disclaimer, the term of this patent is extended or adjusted under 35 U.S.C. 154(b) by 1312 days.

(21) Appl. No.: 11/022,504

(22) Filed: Dec. 21, 2004

(65) Prior Publication Data

US 2005/0149026 A1    Jul. 7, 2005

Related U.S. Application Data

(60) Provisional application No. 60/531,657, filed on Dec. 22, 2003.

(51) Int. Cl.
*A61B 17/80* (2006.01)

(52) U.S. Cl. .......................................... 606/289; 606/71

(58) Field of Classification Search .......... 606/280–299, 606/70, 71
See application file for complete search history.

(56) References Cited

U.S. PATENT DOCUMENTS

| | | | |
|---|---|---|---|
| 2,401,856 A | 6/1946 | Brock | |
| 3,741,205 A | 6/1973 | Markolf et al. | |
| 4,388,921 A * | 6/1983 | Sutter et al. | 606/71 |
| 4,794,918 A * | 1/1989 | Wolter | 606/295 |
| 4,808,185 A | 2/1989 | Penenberg et al. | |
| 5,364,399 A * | 11/1994 | Lowery et al. | 606/295 |
| 5,534,027 A | 7/1996 | Hodorek | |
| 5,951,558 A | 9/1999 | Fiz | |

(Continued)

FOREIGN PATENT DOCUMENTS

CH    674927 A5    8/1990

(Continued)

OTHER PUBLICATIONS

PCT International Search Report relating to International Application No. PCT/US04/43172, date of mailing of the International Search Report, Nov. 1, 2005 (4 pgs.).

*Primary Examiner* — Thomas C. Barrett
*Assistant Examiner* — Michael Araj
(74) *Attorney, Agent, or Firm* — Foley & Lardner LLP

(57) ABSTRACT

A cervical bone plate includes a graft window that allows access to and/or visualization of a bone graft area of the cervical spine after attachment of the present cervical plate to the vertebrae. The window is preferably, but not necessarily, sized for maximum exposure of the graft area and/or the vertebral body without compromising plate strength, particularly with respect to federal standards for such devices. The window is centrally positioned on the plate and is sized to provide alignment of the plate onto the vertebrae at the base of the vertebra fastener or screw holes of the plate. In a dynamic form of this cervical bone plate, the graft window expands and contracts with respective expansion and contraction of the dynamic plate after attachment to the vertebrae (i.e. "dynamizes"). In another form, a three-component dynamic bone plate is configured such that a middle component accepts an identical end component at both ends of the middle component. The end component is a 180° interchangeable part. The middle component and the end component have cooperating configurations and complementarily configured grooves that allow sliding movement between the middle component and the end components. A two-pillar construction provides a central window.

15 Claims, 11 Drawing Sheets

U.S. PATENT DOCUMENTS

| | | |
|---|---|---|
| 6,139,550 A | 10/2000 | Michelson |
| 6,152,927 A | 11/2000 | Farris et al. |
| 6,193,721 B1 | 2/2001 | Michelson |
| 6,224,602 B1 | 5/2001 | Hayes |
| 6,228,085 B1 | 5/2001 | Theken et al. |
| 6,235,034 B1 | 5/2001 | Bray |
| 6,258,089 B1 | 7/2001 | Campbell et al. |
| 6,273,889 B1 | 8/2001 | Richelsoph |
| 6,306,136 B1 | 10/2001 | Baccelli |
| 6,364,881 B1 | 4/2002 | Apgar et al. |
| 6,398,783 B1 | 6/2002 | Michelson |
| 6,402,756 B1 | 6/2002 | Ralph et al. |
| 6,413,259 B1 | 7/2002 | Lyons et al. |
| 6,428,542 B1 | 8/2002 | Michelson |
| 6,454,769 B2 | 9/2002 | Wagner et al. |
| 6,503,250 B2 | 1/2003 | Paul |
| 6,533,786 B1 | 3/2003 | Needham et al. |
| 6,599,290 B2 | 7/2003 | Bailey et al. |
| 6,602,257 B1 | 8/2003 | Thramann |
| 6,620,163 B1 | 9/2003 | Michelson |
| 6,669,700 B1 | 12/2003 | Farris et al. |
| 6,695,846 B2 | 2/2004 | Richelsoph et al. |
| 6,974,460 B2 | 12/2005 | Carbone et al. |
| 2001/0041894 A1 | 11/2001 | Campbell et al. |
| 2002/0045896 A1 | 4/2002 | Michelson |
| 2002/0045899 A1 | 4/2002 | Errico et al. |
| 2002/0111630 A1 | 8/2002 | Ralph et al. |
| 2002/0120273 A1 | 8/2002 | Needham et al. |
| 2002/0128655 A1 * | 9/2002 | Michelson ................ 606/70 |
| 2002/0143336 A1 | 10/2002 | Hearn |
| 2002/0147450 A1 | 10/2002 | LeHuec et al. |
| 2002/0151899 A1 | 10/2002 | Bailey et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0023242 A1 | 1/2003 | Harrington, Jr. |
| 2003/0040749 A1 | 2/2003 | Grabowski et al. |
| 2003/0060828 A1 | 3/2003 | Michelson |
| 2003/0083658 A1 | 5/2003 | Hawkes et al. |
| 2003/0105462 A1 | 6/2003 | Haider |
| 2004/0034356 A1 | 2/2004 | LeHuec et al. |
| 2004/0068319 A1 | 4/2004 | Cordaro |
| 2004/0087951 A1 | 5/2004 | Khalili |
| 2004/0102773 A1 | 5/2004 | Morrison et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127899 A1 | 7/2004 | Konieczynski et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204712 A1 | 10/2004 | Kolb et al. |
| 2004/0220571 A1 | 11/2004 | Assaker et al. |
| 2004/0220572 A1 | 11/2004 | Michelson |
| 2004/0236335 A1 | 11/2004 | Michelson |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0043732 A1 | 2/2005 | Dalton |
| 2005/0059971 A1 | 3/2005 | Michelson |
| 2005/0075633 A1 | 4/2005 | Ross |

FOREIGN PATENT DOCUMENTS

| | | |
|---|---|---|
| DE | 29 33 141 A1 | 4/1980 |
| EP | 0 179 695 A1 | 4/1986 |
| EP | 0 313 762 A1 | 5/1989 |
| FR | 2 651 996 A3 | 3/1991 |
| WO | WO 91/03994 A1 | 4/1991 |
| WO | WO 95/30389 A1 | 11/1995 |
| WO | WO 96/03096 A1 | 2/1996 |
| WO | WO 96/23457 A1 | 8/1996 |

* cited by examiner

STATIC AND DYNAMIC CERVICAL PLATES AND CERVICAL PLATE CONSTRUCTS

This U.S. non-provisional patent application claims the benefit of and/or priority to U.S. provisional patent application Ser. No. 60/531,657 filed Dec. 22, 2003 entitled "Static and Dynamic Cervical Plate Construct", the entire contents of which is specifically incorporated herein by reference.

BACKGROUND OF THE INVENTION

1. Field of the Invention

The present invention relates generally to devices for the internal fixation of the spine particularly within the fields of orthopedics and/or neurosurgery such as spinal implants for holding vertebral bones fixed relative to one another and, more particularly, to static and/or a dynamic bone fixation implants for use in spinal surgical procedures for stabilizing the relative motion of, temporarily or permanently immobilizing, bones of the spine.

2. Background Information

Cervical plates have been used for more than 20 years to increase neck stability following single and multi-level cervical surgery. Cervical plates, implanted during surgery for reasons such as disease, trauma, defect, accident or the like, are used to stabilize one or more cervical vertebrae. Stabilization leads to a proper healing or a desired outcome. The cervical plate is mounted to one or more vertebrae during the surgery. Typically, screws are used to mount the cervical plate to the one or more vertebrae. It is important during the mounting process that the plate be properly aligned on the vertebrae for receipt of the mounting screws.

In some instances, it is desirous to cause the fusion of two adjacent vertebrae. If this is the case, the surgeon makes a small incision in the front of the neck to reach the cervical spine. Tissues and muscles are retracted (spread apart) to reveal the proper level in the cervical spine. The cartilaginous material or disc between the two vertebrae is removed and the bone surface abraded to encourage a bleeding surface. Blood from the bleeding surfaces is desired in order for the bones to fuse. The space between the adjacent vertebrae is filled with bone graft. A cervical plate is then screwed into the superior (top) and inferior (bottom) vertebrae. This stabilizes the cervical spine to facilitate fusion and healing. With current cervical plates however, once the plate is secured over the graft area, the only manner of accessing the graft area is to remove the plate. Moreover, with current cervical plates, it is necessary to provide the bone graft material before mounting the plate.

Heretofore, cervical plates were almost exclusively static, in that they have fixed dimensions. It has been realized that it is desirable in certain situations to allow shifting or slight movement between the plate-mounted vertebrae. The prior art is relatively devoid of dynamic cervical plates.

It is thus evident from the above that what is needed is a cervical plate that allows access to a bone graft area of a cervical surgical site.

It is thus evident from the above that what is needed is a cervical plate that is dynamic.

This need and others are accomplished through application of the principles of the subject invention and/or as embodied in one or more various forms and/or structures such as are shown and/or described herein.

SUMMARY OF THE INVENTION

According to an aspect of the invention, a bone plate is contoured to conform to the shape of typical vertebra or vertebrae when the bone plate is mounted to the vertebra or vertebrae. The bone plate, in one form, is contoured to conform to contours of one or more vertebrae upon anterior placement of the bone plate onto the one or more vertebrae. In one embodiment, the bone plate is contoured in two planes.

According to another aspect of the invention, a cervical bone plate includes an opening or window that allows access to and/or viewing of a bone graft area of the spine after attachment of the cervical plate to the vertebrae. The window is preferably, but not necessarily, sized for maximum exposure of the graft area and/or the vertebral body without compromising plate strength, particularly with respect to federal standards for such devices. The window is centrally positioned on the plate. The graft window is also preferably sized to provide alignment of the plate onto the vertebrae at the base of the vertebra fastener or screw holes of the plate. In a dynamic form of this cervical bone plate, the graft window expands and contracts with respective expansion and contraction of the dynamic plate after attachment to the vertebrae (i.e. "dynamizes").

In one form of the invention, a three-component dynamic bone plate is configured such that a middle component accepts an identical end component at both ends of the middle component. The end component may be a 180° interchangeable part. The middle component and the end component have cooperating configurations and complementarily configured channels that allow sliding movement between the middle component and the end components. A two-pillar construction provides a central window.

As well, in another form of the invention, there is provided a kit for assembling an n-level dynamic cervical plate. The kit includes an extension component and two, identical end components. The end components may be slidingly assembled to each other to provide a dynamic one level (1-L) cervical plate that includes a central window. The end components may be slidingly assembled to each end of the extension component to provide a dynamic two level (2-L) cervical plate that includes two central windows, one between each level. Moreover, the extension component is configured such that two or more extension components may be utilized, 180° rotated each relative to the other. End components may then be assembled to the open ends of the extension component.

The present invention also provides a cervical plate construct comprising a plate formed as a single piece in the case of a static plate, and formed as two or more sections in the case of a dynamic plate, a minimum of four bone screws, and one or more locking covers depending on the level of the cervical plate. The present cervical plate may be formed as a single level plate or a multi-level plate while still retaining the characteristics described and shown herein.

The dynamic plate in accordance with the principles of the subject invention provides for pure vertebral body translation without creating guesswork with respect to screw positioning. The dynamic plate may be fabricated in 1-L or multi-L configurations. Moreover, the dynamic plate utilizes a dual pillar style of plate adjustment. In one form, the dynamic plate is formed of two identical sections situated at 180° relative to one another. The section has two legs, one defining a configured channel or bore therein, and the other having a like configured arm that fits into the channel.

The present invention provides advantages over the teachings of the prior art with respect to cervical plating technology. The principles accompanying the present invention allows the fixation plate to be used with greater accuracy. This may ultimately increase the efficacy of an established procedure. For instance the present invention provides a window within the center area of the plate. This allows viewing of graft material during and after placement. This is accomplished by utilizing a dual pillar configuration for both the static and dynamic plates, and for all levels (1-L, ML) of fixation plates.

BRIEF DESCRIPTION OF THE DRAWINGS

The above mentioned and other features and objects of this invention, and the manner of attaining them, will become more apparent and the inventions will be better understood by reference to the following description of embodiments of the inventions taken in conjunction with the accompanying drawings, wherein.

Figure 1:
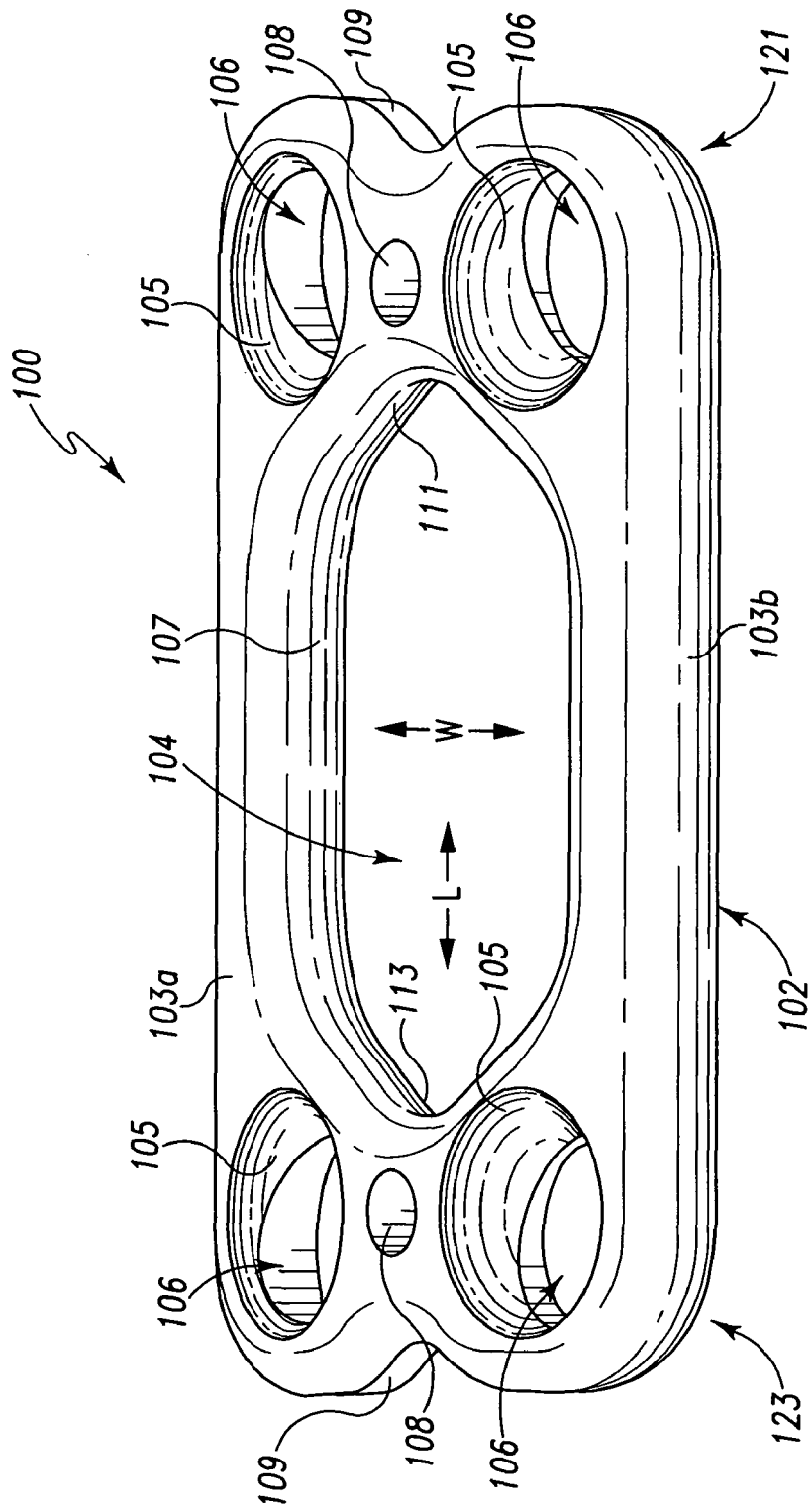
FIG. 1 is a perspective view of an exemplary embodiment of a one-level (1-L) static bone fixation plate fashioned in accordance with the principles of the present invention.

Corresponding reference characters indicate corresponding parts throughout the several views. Although the drawings represent various embodiments of the invention, the drawings are not necessarily to scale and certain features may be exaggerated in order to better illustrate and explain the invention. Also, the exemplifications set out herein illustrate various embodiments of the invention, but such exemplifications are not to be construed as limiting the scope of the invention in any manner.

DETAILED DESCRIPTION OF THE INVENTION

Figure 2:
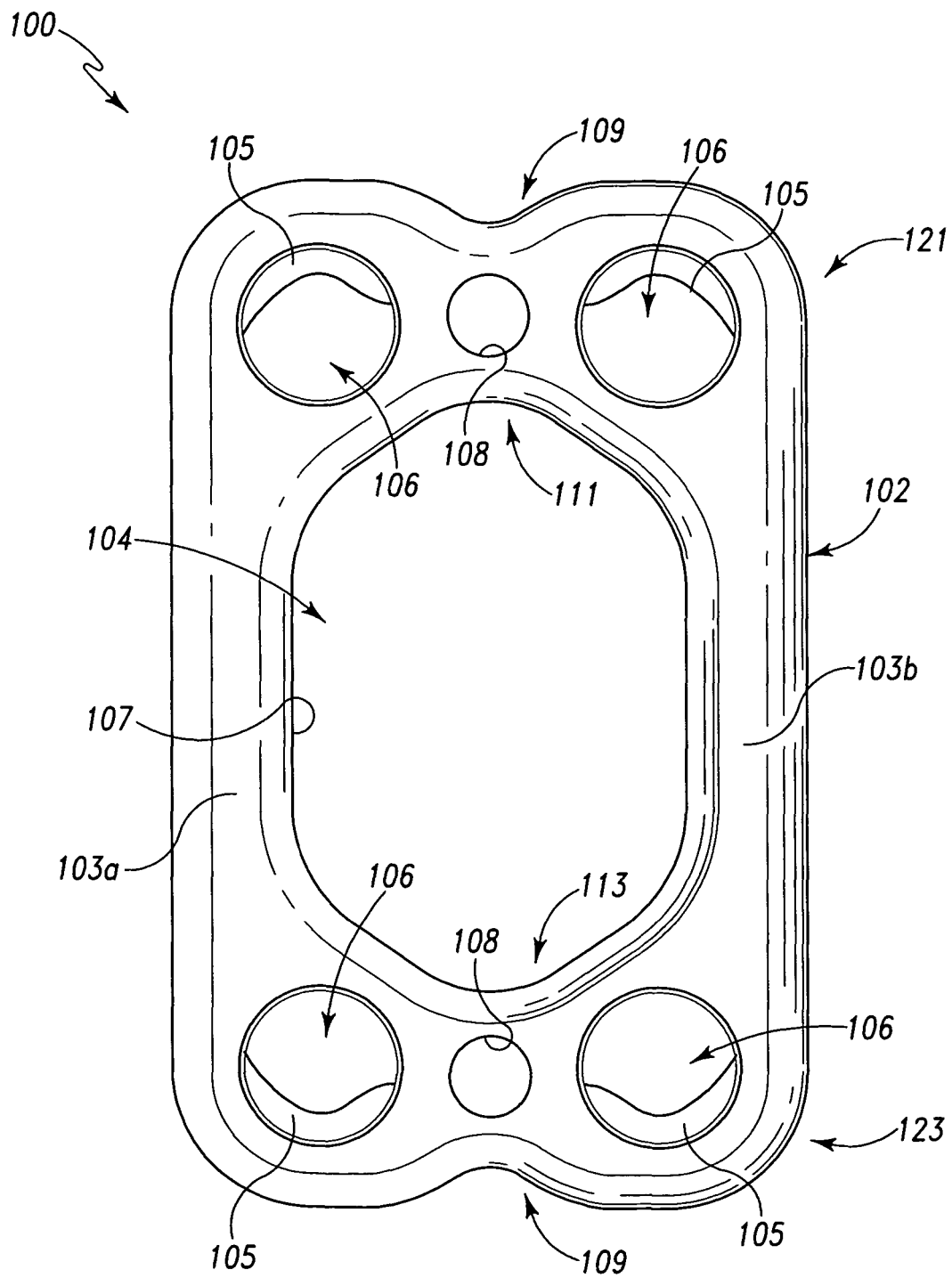
FIG. 2 is a bottom view of the one-level (1-L) static bone fixation plate of FIG. 1.

Referring to FIGS. 1 and 2, there is depicted an exemplary one level (1-L), static cervical plate generally designated 100, of which FIG. 1 is lateral perspective view of the plate 100 and FIG. 2 is a bottom plan view of the plate 100. The plate 100 is characterized by a body 102 formed of a suitable material such as is known for the manufacture of cervical plates, for example titanium, a titanium alloy or the like. The body 102 is generally rectangular in shape and slightly curved on the underside thereof in order to mimic the natural curvature of a vertebra. Such curvature may be in one or two planes. The body 102 may be manufactured in various sizes to accommodate vertebra of different sizes.

The body 102 has an opening, window, void or the like 104 (collectively hereinafter, window) in a middle, center or central portion of the body 102 bounded by surface 107. While the window 104 may be formed in various configurations, it is preferable that the window extend essentially from proximate to adjacent bone screw bores 106 that are situated on ends 121, 123 of the 1-L plate 100. In the exemplary plate 100, the window 104 is configured in a somewhat oblong shape defining a first peak 111 and a second peak 113. As developed more fully below, the elongation of the window allows for better alignment of the plate 100 on the vertebra by the surgeon. The window 104 itself provides visualization of the bone graft abutment to the posterior section of the plate while in situ. The opening 104 defines a first leg 103a and a second leg 103b to the body 102 that extend between ends 121 and 123 of the body 102. The length (l) is longer then the width (w) of the opening 104. The length (l) is elongated or extended to span essentially between the edges of each screw bore 106.

The window/leg configuration creates a "dual pillar" like support foundation for plate strength as between the first and second ends 121, 123, such as against twisting or flexing. The size and configuration of the window 104 (forming two legs or a dual pillar configuration) provides an easy bone screw placement and/or allows for bone graft viewing. Each leg 103a/103b preferably, but not necessarily, has the same cross-sectional profile. Moreover, the cross-sectional profile of each leg is preferably, but not necessarily, consistent throughout its length between ends 121, 123. Furthermore, the legs 103a/103b have the same height profile as the overall plate body 102.

The ends 121 and 123 each have two bone screw bores 106 each one of which is disposed on corners of the respective ends. The four bone screw bores 106 are preferably, but not necessarily, aligned to correspond to vertices of a rectangle, the rectangle preferably, but not necessarily, being a scaled version of the rectangular body 102. The scaled rectangle forming a pattern for placement of screw bores on a patient's vertebra. The ends 121 and 123 each have an outer contour that defines a notch 109. Each bone screw bore 106 is sized, configured and/or situated such that a portion thereof is adjacent a proximate portion of the opening 104.

Each bone screw bore 106 has a ledge 105 formed in the interior thereof. The ledge 105 is configured to capture an undersurface of a head of a bone screw. As such, each ledge 105 is somewhat dish-shaped to accommodate the complementary shape of the undersurface of the bone screw head. Each ledge 105 is also angled to allow the inserted bone screw to achieve a proper orientation during implantation. The bone screw bores 106 are configured to utilize various types of bone screws such as fixed angle screws, emergency screws, and variable angle screws, examples of which are incorporated herewith through the parent provisional application. Moreover, the bore/ledge allows variable bone screw angulation while fixing or mounting the plate to the vertebrae. Such angulation is up to 30° cephalad—caudal, and 20° lateral—medial.

The body 102 further includes two bores 108 each one of which is situated proximate (here shown as between) bone screw bore pairs 106 of each end 121 and 123. Each bore 108 is configured to receive a boss or fastening device/portion of a bone screw retainer device, cover plate, retention clip, or the like such as described herein for preventing rotation and/or backout of a bone screw that has been implanted.

Figure 3:
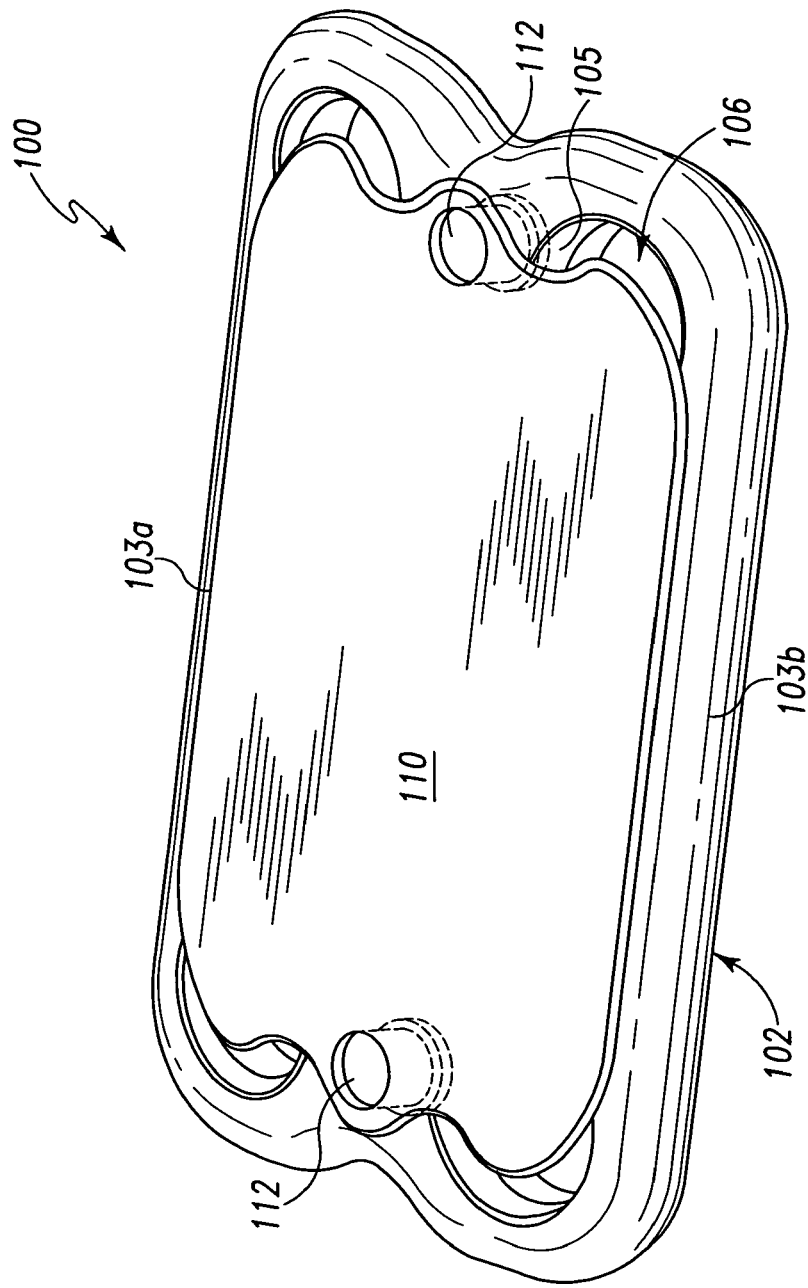
FIG. 3 is a perspective view of the one-level (1-L) static bone fixation plate of FIG. 1 but having a cover thereon fashioned in accordance with an aspect of the present invention.

Referring to FIG. 3, there is depicted the 1-L static cervical plate 100 of FIGS. 1 and 2, but shown with one embodiment of a bone screw anti-backout, rotation inhibitor and/or releasable locking mechanism, embodied as a cover, plate or the like 110. The cover 110 is situated on the plate 100 so as to cover the graft window 104 and at least partially the heads of the implanted bone screws. The cover 110 is used with the plate 100 to provide an embodiment of a 1-L static cervical plate construct. After the plate 100 has been implanted through use of bone screws, such as via the procedure described herein, the cover 110 may be placed onto the body 102. This covers the opening 104, and most of the screw bores 106. The cover 110 is essentially flat, thus having a low profile.

The cover 110 moreover surrounds the window 104 and most of each bone screw bore 106 (which would be most of a bone screw head when so installed). This helps to keep, retain or releasably lock the bone screws from backing out and/or turning. The cover also will provide protection against potential graft migrating out of the inter-vertebral space post operatively. The cover further will allow for post-operative visualization via radiograph. The cover 110 includes two cover bosses 112 that are configured to provide a snap fit into plate bores 108 when installed, such that the cover 110 is retained on the plate 100. While normal use will not cause the cover 110 to separate from body 102, a simple tool may allow removal of the cover 110.

The cover 110 is exemplary of the type of covers that may be used as bone screw locking mechanisms with the 1-L static cervical plate 100. As such, covers 110 may be manufactured in various sizes to accommodate various sizes of cervical plates 110. The cover 110 is also fabricated from a biocompatible material like the material for the plate 100. The plate 100 may also accommodate other styles of covers.

Figure 4:
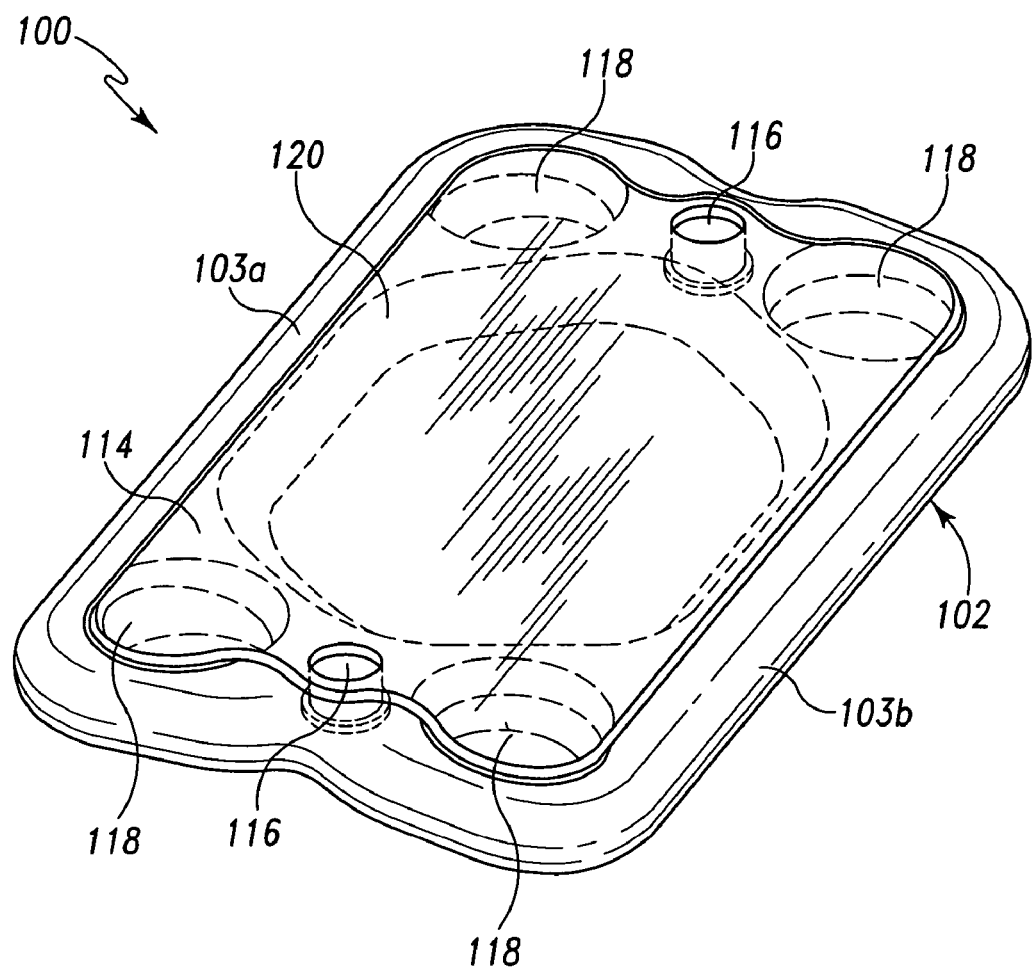
FIG. 4 is a perspective view of the one-level (1-L) static bone fixation plate of FIG. 1 having a contoured cover thereon fashioned in accordance with an aspect of the present invention.

FIG. 4 depicts an alternative cover 114 (bone screw locking mechanism and/or graft window/area cover) for the 1-L static cervical plate 100 of FIG. 1. The cover 114 includes two bosses 116 that are configured to be snap fit received in the plate bores 108 thus retaining the cover 114 onto the plate 100. The cover 114 extends over the opening 104 of the plate from over the leg 103a to over the leg 103b, and over each screw bore 106 of the body 102.

In this embodiment, the cover 114 includes a depression or concavity 120 that is configured like the opening 104 in order to extend into the opening 104 when the cover 114 is installed. Moreover, the cover 114 includes four screw bore depressions or concavities 118 each of which is configured to extend into one of the bone screw bores 106 of the body 102 of the plate 100. The covers or cover plates may be fashioned from an alloy of metals, titanium, a titanium alloy, PEEK, or suitable biocompatible material.

While none of FIGS. 1-4 show a bone screw in use with the plate 100, it should be appreciated that the plate 100 is able to utilize various types of bone screws such as were set forth in the corresponding provisional application, incorporated above. Briefly, the plate 100 may utilize a polyaxial bone screw, a fixed bone screw, and an emergency bone screw.

Figure 5:
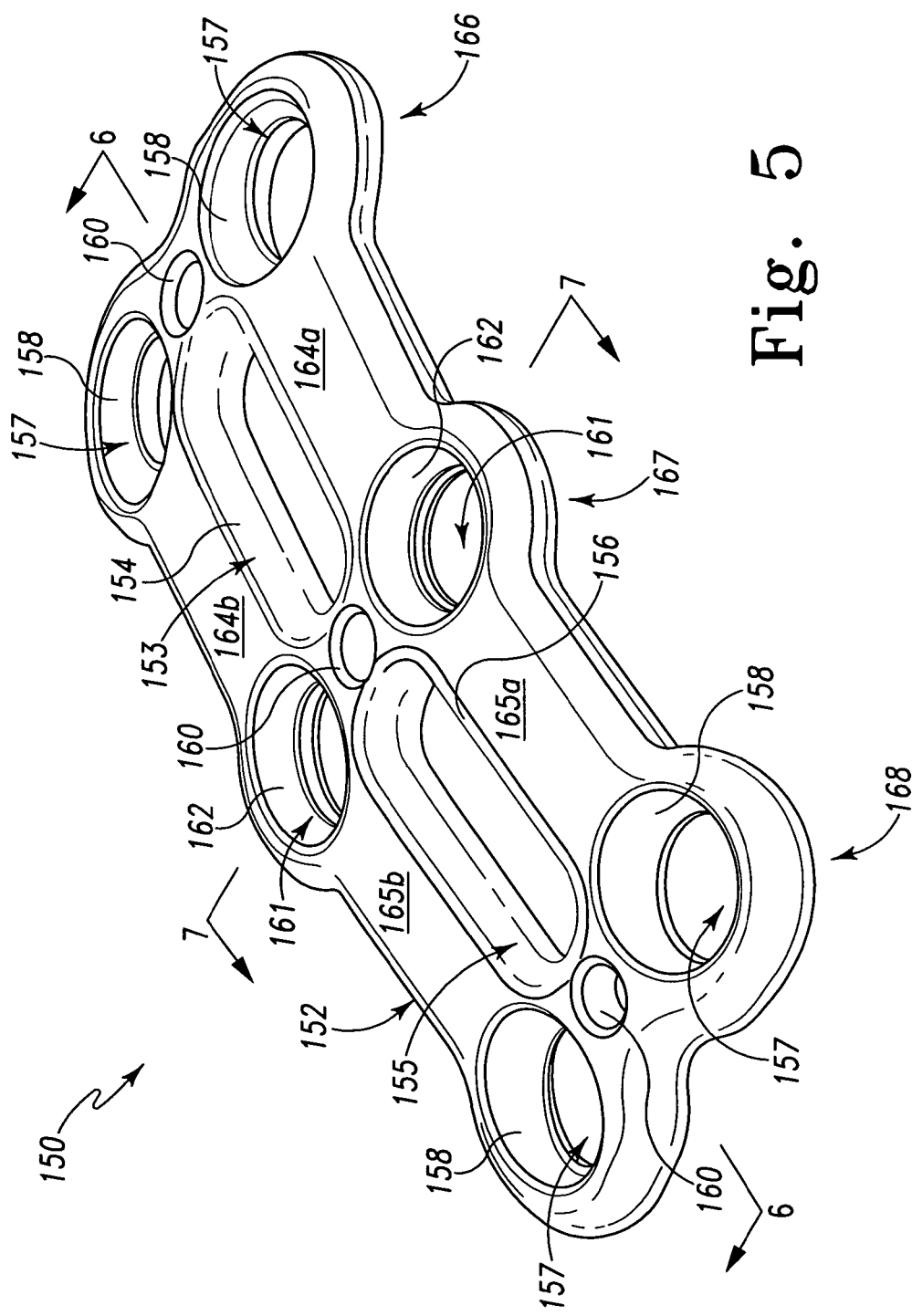
FIG. 5 is a perspective view of an exemplary embodiment of a two-level (2-L) static bone fixation plate fashioned in accordance with the principles of the present invention.
Figure 6:
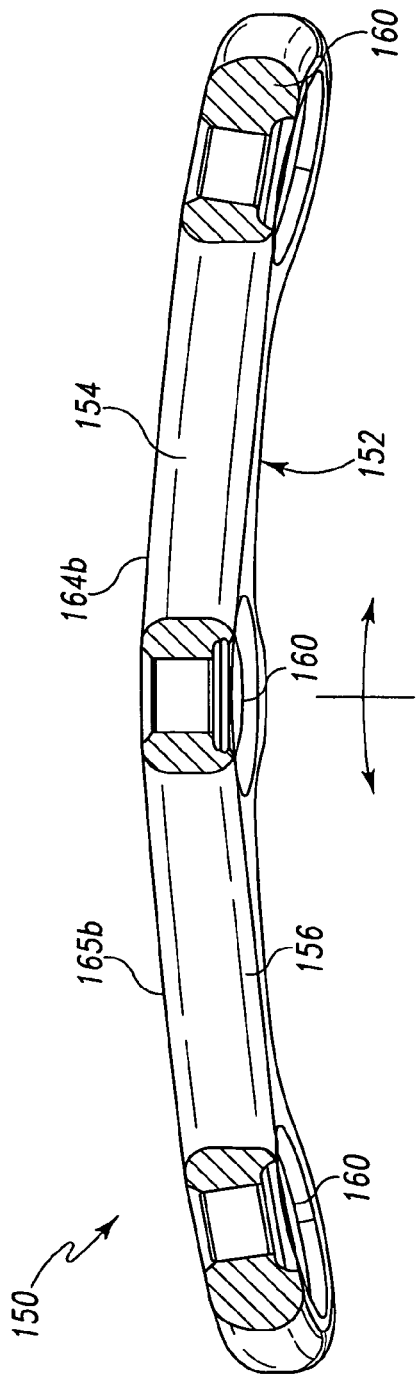
FIG. 6 is a sectional view of the 2-L static bone fixation plate of FIG. 5 taken along line 6-6 thereof.
Figure 7:
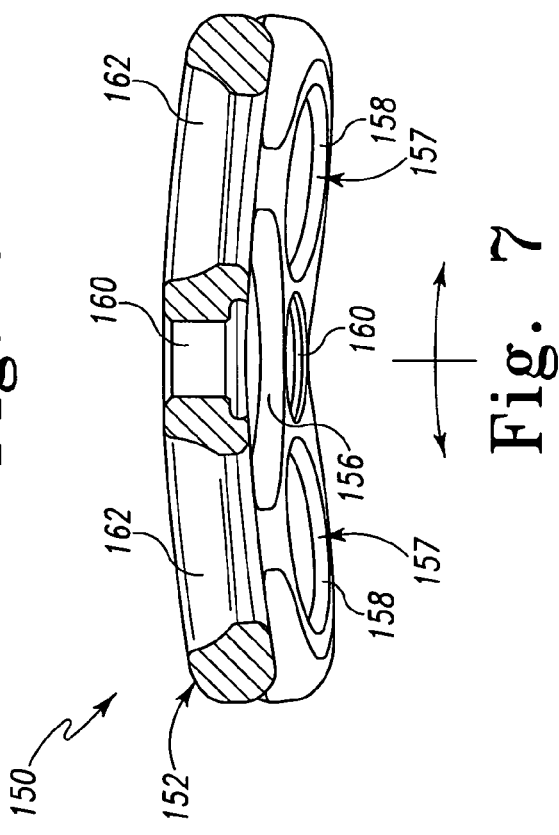
FIG. 7 is a sectional view of the 2-L static bone fixation plate of FIG. 5 taken along line 7-7 thereof.

Referring now to FIGS. 5-7, there is depicted an exemplary embodiment of a two level (2-L) static cervical plate, generally designated 150, incorporating the dual or twin pillar configuration for each level thereof such as described with reference to the 1-L plate 100. The 2-L plate is designed to span between and be anchored to three vertebrae with a central window in accordance with the present principles between each fastening juncture thereof. The windows formed by the dual pillar configuration. As indicated in FIGS. 6 and 7 by the curved arrow relative to a horizontal line (representing a centerline of the plate 100) illustrates two planes of curvature that the plate 100 may have mimicking the curvatures of vertebrae. As such, a particular length and/or thickness cervical plate may also be manufactured with varying curvatures.

The plate 150 is defined by a body 152 that may be considered as having a middle portion or section 167, a first end portion or section 166 on one side of the middle portion 167, and a second end portion or section 168 on another side of the middle portion 167. The middle portion 167 defines a fastening, mounting or attachment portion that is adapted to be attached to a central vertebra of a three vertebrae fusion. The end portions 166 and 168 also define a fastening, mounting or attachment portion that is adapted to be attached to separate outer vertebra of the three vertebrae fusion. As such, and keeping with the principles set forth herein with respect to the 1-L static plate 100, the static 2-L plate 150 includes dual (two) openings, windows, voids or the like 153 and 155, one opening for each level or between each end portion 166, 168 and the middle portion 167. Each window 153 and 155 is centrally, located defines leg pairs (pillars) 164a/164b and 165a/165b.

The opening 153 is disposed in the middle, center or central portion of the area between the end portion 166 and the middle portion 167, being bounded by surface 154. The window 153 is configured in an exemplary fashion as an elongated oval that extends from just adjacent to a portion of each screw bore 157 of the end portion 166 (proximate the reception bore 160 of the end portion 166) to just adjacent to a portion of each screw bore 161 of the middle portion 167 (proximate the reception bore 160 of the middle portion 167).

The opening 155 is disposed in the middle, center or central portion of the area between the end portion 168 and the middle portion 167, being bounded by surface 156. The opening 155 is configured as an elongated oval that extends from just adjacent to a portion of each screw bore 157 of the end portion 168 (proximate the reception bore 160 of the end portion 168) to just adjacent to a portion of each screw bore 161 of the middle portion 167 (proximate the reception bore 160 of the middle portion 167).

The elongation of the openings 153, 155 allow for alignment of the plate 150 during surgery and mounting thereof by the surgeon. The size and configuration of the openings 153, 155 (forming two legs or a dual pillar configuration) provides easy bone screw placement and/or allows for bone graft viewing.

Each leg pair 164a/164b and 165a/165b preferably, but not necessarily, has the same cross-sectional profile. As well, each leg 164a/b and 165a/b preferably, but not necessarily has the same cross-sectional profile. Moreover, the cross-sectional profile of each leg is preferably, but not necessarily, consistent throughout its length between the middle portion 167 and end portions 166 and 168. Furthermore, the legs 164a/b and 165a/b have the same height profile as the overall plate body 152.

The ends 166 and 168 each have two bone screw bores 157 each one of which is disposed on corners of the respective ends and at least partially defining the fastening portions. The ends 166 and 168 each have an outer contour that defines a notch. Each bone screw bore 106 is sized, configured and/or situated such that a portion thereof is adjacent a proximate portion of its respective opening 153, 155. Each bone screw bore 157 has a ledge 158 formed in the interior thereof. Each ledge 158 is configured to capture an undersurface of a head of a bone screw. As such, each ledge 158 is somewhat dish-shaped to accommodate the complementary shape of the undersurface of the bone screw head. Each ledge 158 is also angled to allow the inserted bone screw to achieve a proper orientation during implantation. The bone screw bores 157 are configured to utilize various types of bone screws as described above. Additionally, the bone screw bores 157 are configured to utilize various types of bone screws such as fixed angle screws, emergency screws, and variable angle screws, examples of which are incorporated herewith through the parent provisional application. Moreover, the bore/ledge allows variable bone screw angulation while fixing or mounting the plate to the vertebrae. Again, such angulation may be up to 30° cephalad—caudal, and 20° lateral—medial.

The middle portion 167 also has two bone screw bores 161 disposed as pairs of screw bores in like manner to the other screw bores at least partially defining the fastening portion. Each bone screw bore 161 is sized, configured and/or situated such that a portion thereof is adjacent a proximate portion of an opening 153, 155. Each bone screw bore 161 has a ledge 162 formed around the interior thereof. Each ledge 162 is configured to capture an undersurface of a head of a bone screw. As such, each ledge 158 is somewhat dish-shaped to accommodate the complementary shape of the undersurface of the bone screw head. Each ledge 158 is also designed to receive the inserted bone screw in a fairly straight manner to achieve a proper orientation during implantation. The bone screw bores 161 are configured to utilize various types of bone screws like those above.

The body 152 further includes two bores 160 each one of which is situated between bone screw bore pairs 157 of each end portion 166 and 168. An additional like bore 160 is positioned in the middle portion 167. Each bore 160 is configured to receive a boss or fastener of a bone screw retainer device, cover plate, retention clip, or the like.

Figure 8:
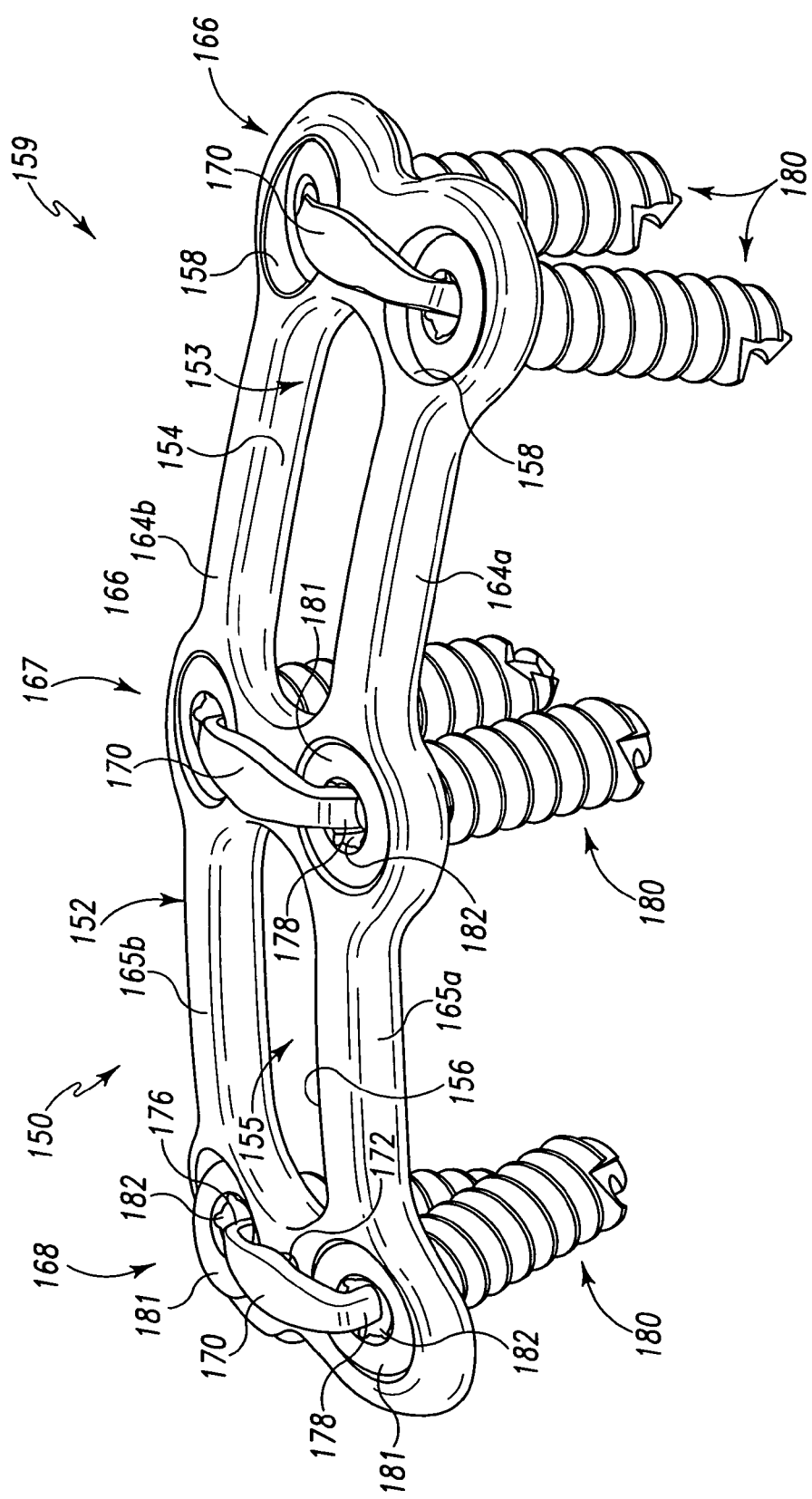
FIG. 8 is a perspective view of a 2-L construct including the 2-L static bone fixation plate of FIG. 5 with bone plate screws and bone screw retention clips.

Referring to FIG. 8, there is depicted an exemplary 2-L static cervical plate construct 159. The 2-L static cervical plate construct 159 includes the 2-L static cervical plate 150, bone screws 180, and bone screw locking, retainer or retention clips, tabs or the like 170 (clips). Some of the bone screws 180 are depicted in various orientations relative to the plate 150 to illustrate the ability of the plate 150 to allow such variable orientations. The construct 159 utilizes releasable bone screw locking means, anti-backing, retainer, retention or retaining clips or tabs 170 that attach onto and between pairs of screws 180, particularly the pairs of screws for each body section 166, 167, 168. The clips 170 also attach to the plate body 152. The clips 170 aid in preventing the backing out or rotation of the bone screws thus providing locking of the bone screws and to the cervical plate.

Figure 9:
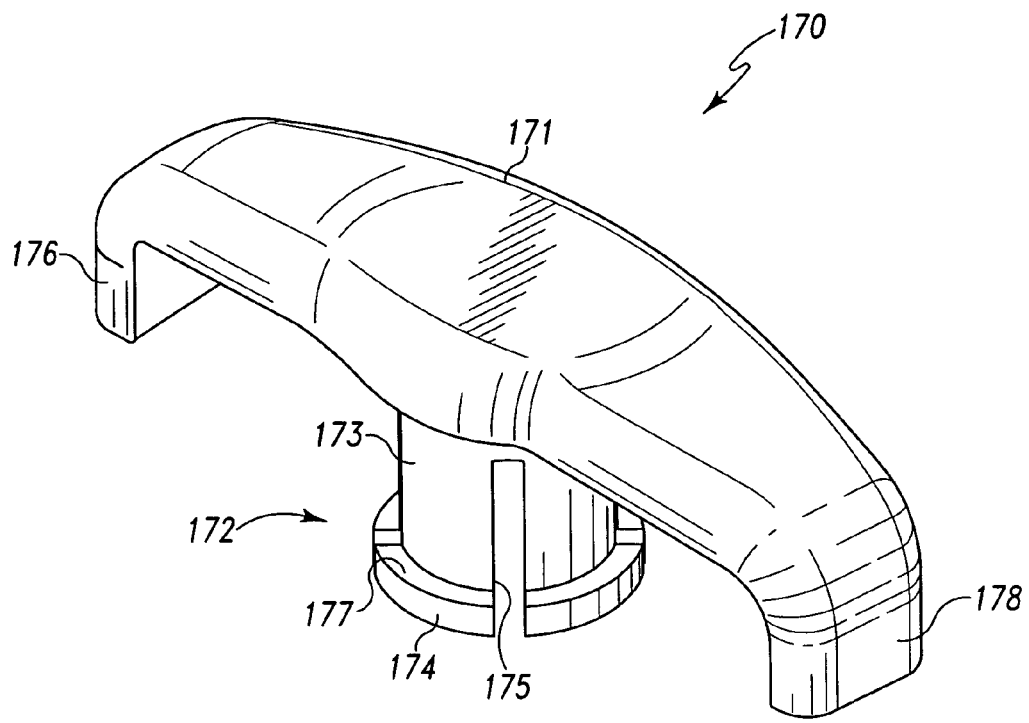
FIG. 9 is an enlarged perspective view of the bone screw retention clip depicted in FIG. 8.

Additionally referring to FIG. 9, a clip 170 is depicted. The clip 170 has been enlarged for clarity. The clip 170 is formed of a biocompatible material preferably, but not necessarily, the same material as the cervical plates and/or cover plates. The clip 170 is defined by a body 171 having a first prong 176 on one end thereof, a second prong 178 on a second end thereof, and a boss structure 172. The body 171 is sized such that the prongs 176 and 178 span the distance between bone screw heads. The boss structure 172 is defined by a post 173 that extends from the underside of the body 171. The post terminates in a rim 174 and includes one or more slots 175. The post 173 is configured to be received in the clip post (boss) bore 160 of the body 152 of the plate 150 (and other such situated bores in the other plates described herein) thus releasably retaining or locking the clip 170 to the plate 150.

Each prong 176, 178 is adapted to be received in a bone screw head socket. It should be appreciated, that the use of clips 170 is not limited to static 2-L plates as shown, but may be used with static 1-L plates, static multi-level plates, and dynamic plates of all levels. The clip 170 is provided in various sizes in order to be used with plates of various sizes, since the span between bone screw heads may be different for different size plates. The clip 170 also has a low profile (thickness) so as to remain relatively flat against the plate 150.

The diameter of the post 173 is slightly less than the diameter of the receiving bore in the plate (e.g. bore 160 of plate 150) so that the receiving bore may receive the post. The rim 174, however, defines a diameter that is oversized for the receiving bore in the plate. The notches or slots 175 allow the ends of the post 173 to slightly compress, reducing the effective diameter of the rim 174, causing the rim 174 to pass through the receiving bore. Once the rim 174 is through the receiving bore, the post 173 returns to its uncompressed state such that the end 177 of the rim 174 contacts the underside of the plate, preventing the clip 170 from pulling out of the receiving bore without a special tool or the like. The resilient boss 174 is thus configured to be releasably, but snugly snap or press fit received into an appropriate plate bore.

The interaction of the clip 170 with the plate 150 and the bone screw pairs is best seen in FIG. 8, and particular attention is drawn to the end portion 168 of the plate 150 of FIG. 8. Each bone screw 180 has a head or head portion 181. Each head 181 includes a socket 182 formed therein. The socket 182 is preferably, but not necessarily, configured in a polygonal pattern. Other configurations may be used. Each corner 182 of the polygon pattern (socket configuration) is rounded such that the span of the ends of the prongs 176, 178 fits into two rounded corners 182. In this manner the prongs 176 and 178 lock the bone screws from rotation. Moreover, rotation of either bone screw of the bone screw pair fitted with a clip 170 will slightly rotate the clip in the plane of the plate 150 thus binding the clip against each other. The clip 170 is also releasably locked to the plate 150.

The boss 172 of the clip 170 is situated in the bore 157 (snap-fit received). One prong 176 extends into the socket 182 of the head 181 of the upper bone screw 180 while the other prong 178 extends into the socket 182 of the head 181 of the lower bone screw 180. The prongs interact with the polygon socket of the head to limit rotation of a screw. The first and second configured flanges 176, 178 are configured to be press or snap fit received in the bone screw head socket.

Figure 10:
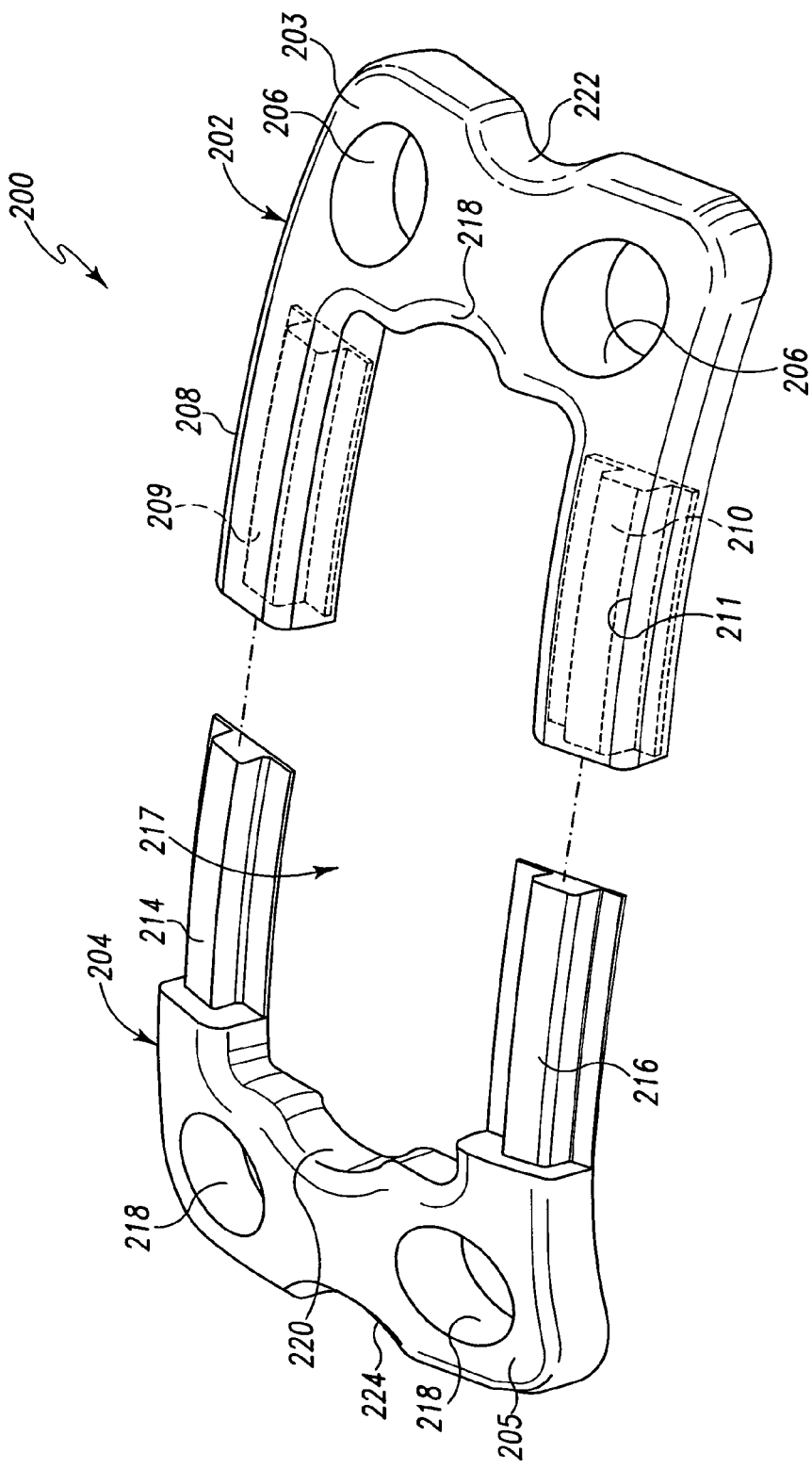
FIG. 10 is a perspective view of an exemplary embodiment of a one-level (1-L) dynamic bone fixation plate fashioned in accordance with the principles of the present invention, the 1-L dynamic plate shown in an almost fully open or fully dynamic state.

FIG. 10 depicts an exemplary embodiment of a dynamic 1-L cervical plate generally designated 200, in accordance with the present principles. The dynamic 1-L plate 200 is shown in exploded form to better illustrate the manner in which the dynamic plate is assembled, joined and/or is dynamic or dynamizes. The dynamic 1-L plate 200 is characterized by a first section 202 and a second section 204 that when assembled or together provides an opening, void or window 117. The size of the opening 117 is variable depending on the position of the two sections 202, 204 relative to one another. Each section 202, 204 defines a U-shape or portion that slidingly mates with one another to provide dynamization when attached. This sliding motion is unconstrained such that it smoothly transitions between various positions without ratchets or the like. The sections 202, 204 each provide a fastening portion, one for each vertebra. The window 217 exposes an area between the vertebrae. It should be appreciated that the configuration of such mating may be modified and/or deviate from that shown.

The first section 202 has a body 203 supporting two bone screw bores 206 which, while not shown, may include configured ledges such as the configured ledges 158 of bone screw bores 157 of plate 150 (see, e.g. FIG. 5) for variable bone screw angulation as described above. The first section 202 also includes first and second legs 208 and 211. The first leg 208 has a configured channel 209 extending therein. The second leg 211 also has a configured channel 210 extending therein. While not necessary, the first and second channels 209, 210 are preferably the same configuration, but may be of one each such that the device is 180° rotatable and be the same.

The second section 204 has a body 205 supporting two bone screw bores 218, which, while not shown, may include configured ledges such as the configured ledges 158 of bone screw bores 157 of plate 150 (see, e.g. FIG. 5). The second section 204 also includes first and second configured arms 214, 216. The first configured arm 214 is configured and/or dimensioned in like manner to the channel 209 and thus to be slidingly receivable into the configured channel 209. The second configured arm 216 is also configured and/or dimensioned in like manner to the channel 210 and thus to be slidingly receivable into the configured channel 211. The arms 214, 216 are of a length to be fully received in the respective channel 209, 211 so the ends of the legs 208, 210 abut the ends of the arms 214, 216. In this manner, the dynamic 1-L plate 200 of FIG. 10 provides relative movement between the two sections or components 202, 204.

Figure 11:
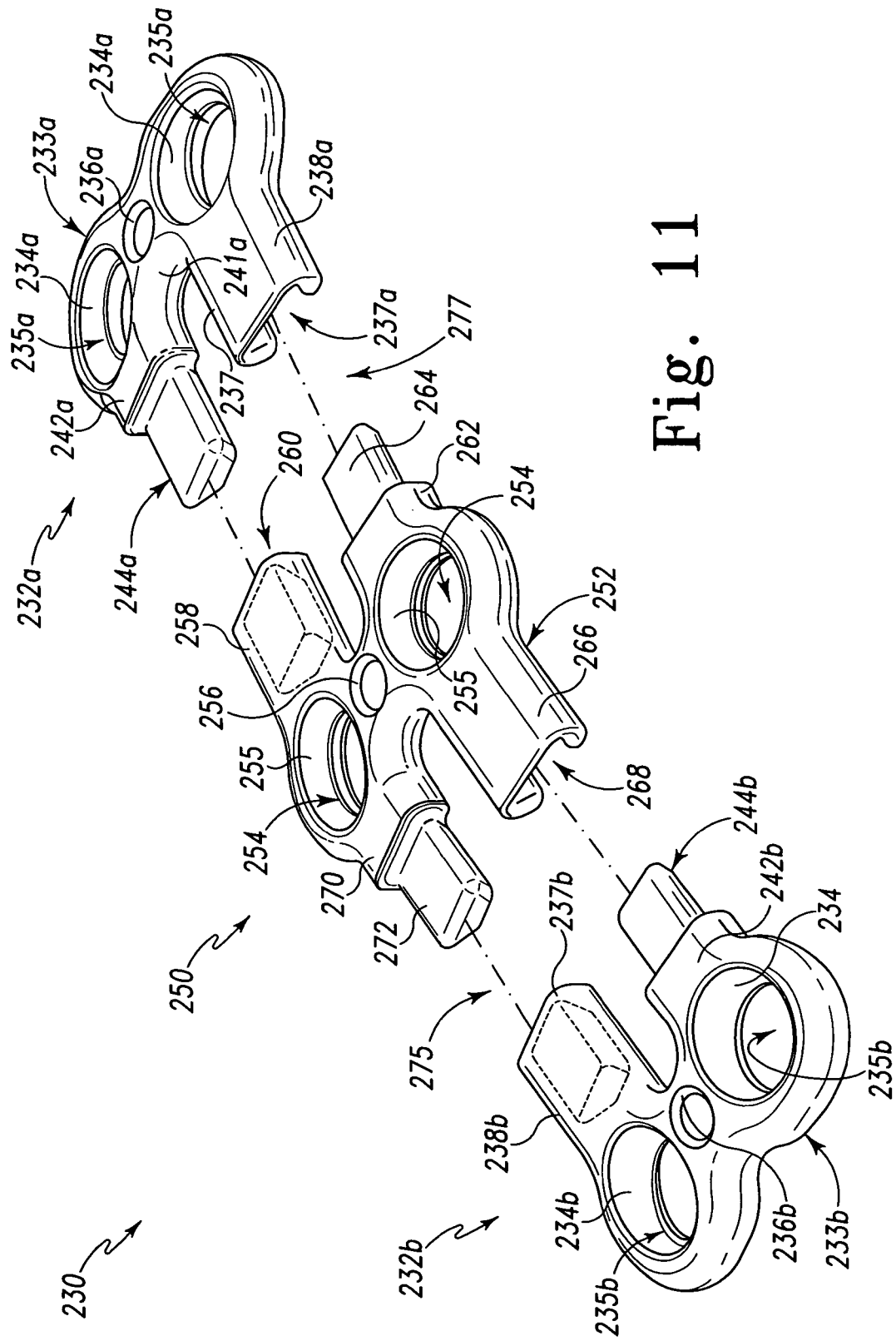
FIG. 11 is a perspective view of an exemplary embodiment of a two-level (2-L) dynamic bone fixation plate fashioned in accordance with the principles of the subject invention, the 2-L dynamic plate shown with each end plate portion of the 2-L dynamic plate in exploded view relative to an intermediate plate portion of the 2-L dynamic plate.

Referring to FIG. 11, there is depicted an exemplary embodiment of a dynamic two level (2-L) plate generally designated 230 formed in accordance with an aspect of the subject invention. The dynamic 2-L plate 230 is shown in exploded form to better illustrate the manner in which the dynamic plate is assembled, joined and/or is dynamic or dynamizes. This also illustrates how the middle plate component 250 may be used with itself to form n-levels of cervical plates with end components (i.e. two end plate components 232 for attachment to beginning and end vertebrae, and n middle plate components 250 defining the n-levels for attachment to n number of middle vertebrae), and moreover with each level providing dynamization (internally dynamizing). Thus, each internal or middle section is dynamizing as between themselves, not just the end plate components relative to a middle portion. The dynamic 1-L plate 200 is characterized by a first section 202 and a second section 204 that when assembled or together provides an opening, void or window 117. The size of the opening 117 is variable depending on the position of the two sections 202, 204 relative to one another. Each section 202, 204 defines a U-shape or portion that slidingly mates with one another to provide dynamization when attached. This sliding motion is unconstrained such that it smoothly transitions between various positions without ratchets or the like. The sections 202, 204 each provide a fastening portion, one for each vertebra. The window 217 exposes an area between the vertebrae. It should be appreciated that the configuration of such mating may be modified and/or deviate from that shown.

As such, the dynamic plate 230 has extended windows or openings formed by the dual pillar structure and, more particularly, has two windows formed by two dual pillar structures. The dynamic plate 230 is a two level (2-L) plate that is composed of three components which are shown in exploded view relative to one another in FIG. 11. The plate 230 is formed of a middle plate component 250 and two end plate components 232a and 232b. The two end plate components 232a and 232b are identical. A 180° reversal of an end component 232, in conjunction with the configuration of the middle component 250, allows the dynamic 2-L plate to utilize only two different pieces. Therefore, kits to provide n-level plates would come with two end plate components, and a plurality of middle plate components.

End component 232a is defined by a body 233a having bone screw bores 235a and configured ledges 234a such as described above. A retention bore 236a for a locking clip 170 or cover plate boss is provided between the two bone screw bores. The body 233a defines a first leg 238a having a configured channel or cutout 237a therein. The shape of the channel 237a provides lateral and up/down stability to a joining or mating piece of the middle component 250. Thus, the configuration of the channel may be changed as appropriate under the present principles. In this particular form, the channel 237a is configured akin to a dovetail. A second leg 244a of the body 233a is configured akin to the channel 237a dovetail. It should be observed that the end components 232a and 232b may be joined or assembled into a dynamic 1L plate without the use of the middle component 250 since the leg 244b (identical to leg 244a) will be received in leg channel 237a while the leg 244a will be received in leg channel 237b (identical to leg channel 237a).

The end component 234b is defined by a body 233b having bone screw bores 235b and configured ledges 234b such as described above. A retention bore 236b for a retention clip or cover boss is provided between the two bone screw bores. The body 233b defines a first leg 238b having a configured channel or cutout 237b therein. The shape of the channel 237b provides lateral and up/down stability to a joining or mating piece of the middle component 250. Thus, the configuration of the channel may be changed as appropriate under the present principles. In this particular form, the channel 237b is configured akin to a dovetail. A second leg 244b of the body 233b is configured akin to the channel 237b dovetail.

The middle or expansion component 250 is defined by a body 252 having two bone screw bores 254 having head seats 255, and a boss bore 256. The body 252 also includes a first leg 258 having a configured channel 260 therein. The channel 260 receives the configured leg 244a of the section 232a (or flange 272 of another expansion component) and is thus configured appropriately. A second leg 262 of the body 252 includes a configured flange 264 that is configured to be received in the channel 237a of the section 230 (or a channel 268 of another expansion component) and is thus configured appropriately. A third leg 270 includes the configured flange 272 receivable in the channel 237b of the section 232b (or in the channel 260 of another expansion component). A fourth leg 266 of the body 252 includes the channel 268 that receives the configured flange 244 of the section 230 or the flange 264 of another expansion device. This structure and/or interrelationship of the middle component 250 to itself and to the end components 232, provides the ability to assemble N-level, dynamic plates. The 2-L dynamic plate 230, when assembled, defines first and second windows, voids or openings 275, 277 between the middle component 250 and each end component 232. The legs and flanges when assembled each have the same cross-section. The truncated triangle cross-section provides loading stability.

Figure 12:
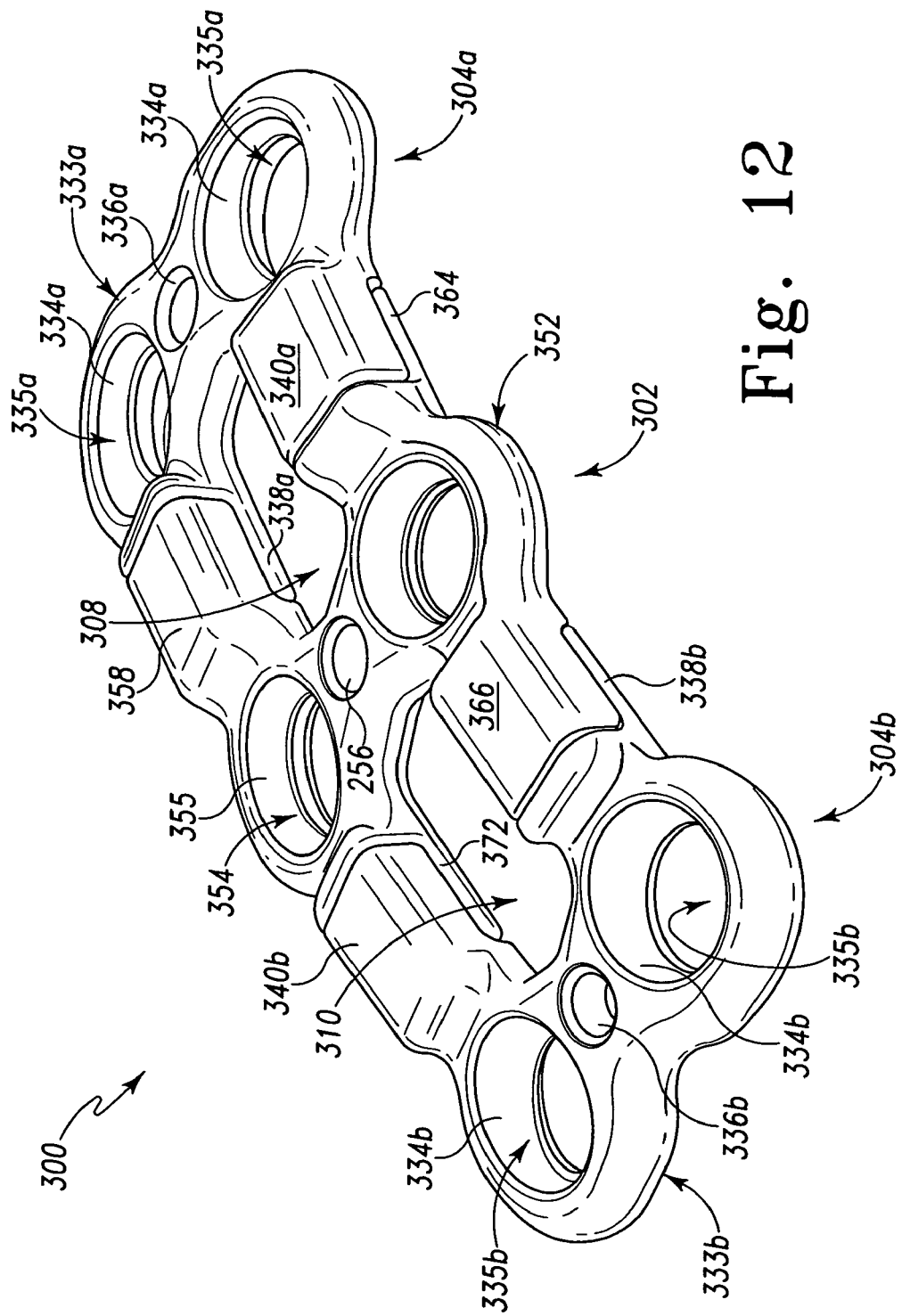
FIG. 12 is a perspective view of an exemplary embodiment of another 2-L dynamic bone fixation plate fashioned in accordance with the principles of the subject invention, the 2-L dynamic plate shown with end plate portions thereof in an exploded position relative to an intermediate plate portion thereof in accordance with the principles of the subject invention.

FIG. 12 depicts another exemplary embodiment of a dynamic two-level cervical plate, generally designated 300, that is a variation of the dynamic two-level cervical plate 230 but which incorporates the features and/or functions of the plate 230. As such, the 2-L plate 300 has components that can be assembled to form a 1-L plate or an n-level plate. The plate 300 is formed of a middle component 302 and first and second identical end components 304a, 304b. Like plate 230, the dynamic plate 300 has extended windows or openings formed by dual pillar structures. The dynamic plate 300 is a two level (2-L) plate that is composed of three components which are shown assembled in FIG. 11. The plate 300 is formed of a middle plate component 302 and two end plate components 304a and 304b. The two end plate components 304a and 304b are identical. A 180° reversal of an end component 304, in conjunction with the configuration of the middle component 302, allows the dynamic 2-L plate to utilize only two different pieces.

End components 304a/b is defined by a body 333a/b having bone screw bores 335a/b and configured ledges 334a/b such as described above. A retention bore 336a/b for a retention clip or cover boss is provided between the two bone screw bores. The body 333a/b defines a first leg 338a/b having a configured mating structure thereon. The body 333a/b also defines a thickened second let 340a/b that has a channel for receiving a like configured leg portion of the middle component 302, the shape of which provides lateral and up/down stability to a joining or mating piece of the middle component 302. Thus, the configuration of the channel may be changed as appropriate under the present principles. It should be observed that the end components 304a and 304b may be joined or assembled into a dynamic 1L plate without the use of the middle component 302.

The middle or expansion component 302 is defined by a body 352 having two bone screw bores 354 having head seats 355, and a boss bore 356. The body 352 also includes a first thickened leg 358 having a channel therein that is configured to receive the configured leg 338a of the end component 304a (or flange 366 of another middle component 350) and is thus configured appropriately. A second leg 364 of the body 352 includes a flange that is configured to be received in the channel structure 340a of the end component 304a (or a channel 366 of another middle component) and is thus configured appropriately. A third leg 372 includes configured flange receivable in the channel structure 340b of the end section 232b (or in the channel of another middle component). A fourth leg 366 of the body 352 includes a channel structure that receives the configured flange 338b of the end component 304b or the flange of another middle component. This structure and/or interrelationship of the middle component 302 to itself and to the end components 304, provides the ability to assemble N-level, dynamic plates. The 2-L dynamic plate 300, when assembled, defines first and second windows, voids or openings 308, 310 between the middle component 302 and each end component 304. The legs and flanges when assembled each have the same cross-section.

The various dynamic plates of the present invention are assembled from a number of end and middle components depending on the desired plate level. The various components are slidingly interconnected to one another. It should be appreciated that once assembled, the plate components, while slidable with respect to each other, have a disassembly stop or constraining mechanism or device such that the plate components will not disassemble once assembled. The disassembly constraining mechanism constrains or limits the length of travel of the leg assemblies (slidingly connected legs of the plate components) of the two plate components relative to one another in a disassembled direction of travel.

Figure 13:
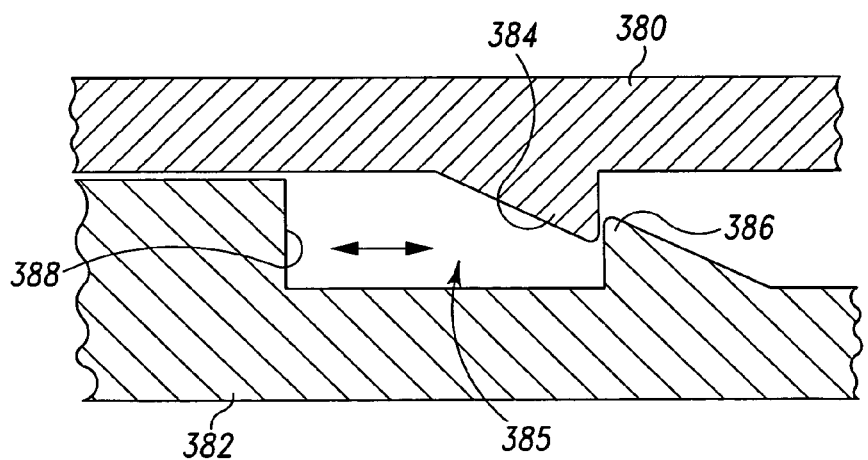
FIG. 13 is an enlarged sectional view of an exemplary constraining mechanism that may be utilized in the present dynamic plates.

To this end and referring to FIG. 13, there is depicted an exemplary disassembly constraining mechanism for the present dynamic plate components. Particularly, FIG. 13 illustrates an enlarged portion of two slidingly interconnected legs 380, 382 of any two assembled dynamic plate components according to the principles of the present invention. Leg 380 may be a configured leg with a channel or groove, while the leg 382 is a configured leg with a flange, or vice versa such as described herein. When referring to FIG. 13, however, the arm 380 will arbitrarily considered a configured channel arm and the arm 382 necessarily considered the configured flange arm. It should also be appreciated that distances and lengths are not necessarily to scale and/or in proportion with one another.

The channeled arm 380 has a detent 384 within the groove (the underside per FIG. 13) of the arm 380. The detent 384 extends a distance from the groove surface into the are 385 and is preferably, but not necessarily, in the form of a right triangle having a sharp to rounded apex. The flanged arm 382 includes a notched or cutout area or portion 385 bounded by a ledge 388. A detent 386, again preferably, but not necessarily in the form of a right triangle having a sharp to rounded apex, is situated within the area 385.

During assembly, the detent 386 is to the left of detent 384. While the height of the detents are such that the apex of each detent extends beyond the apex of the other detent, as the two detents 384, 386 meet their angled or ramped surfaces meet. Continued travel allow the ramps to slide relative to another. The small overlap in detent height thus allows the detent 384 to reside in area 385 once full assembly has taken place. In one direction of travel, the detent 384 will contact ledge 388, while in the other direction the difference in detent height creates a stop. Of course, other types of stop mechanisms may be employed that allow assembly but prevents disassembly or makes disassembly extremely difficult.

The cervical plates described above are intended for anterior screw fixation to the cervical spine (C2 through T1) for various conditions such as at least the conditions of spondylolisthesis, fracture, spinal stenosis, and tumor. Moreover, it should be appreciated that the configuration(s) and/or principles of the 1-L dynamic plate(s) described herein are applicable to and/or may be used in the various 2-L dynamic plates also described herein. As well, 2-L dynamic plate configurations described herein may be used in the 1-L plates described herein. This is particularly true with respect to the various leg or projection configurations and the sliding connectivity thereof.

Each plate is preferably, but not necessarily, formed from titanium (e.g. titanium 6A1-4V ELI per AASTM F-136). Other suitable metals, ceramics may be used if appropriate.

In general, the preferred embodiment of the present cervical plates will embody curvature in two planes (sagittal and coronal) to more closely resemble the anatomical aspects of the spine. The cervical plates may be provided without curvature or with curvature in one plane as necessary. The plates are made in various sizes (e.g. 14 mm through 110 mm) to accommodate various spines. The plates have a nominal thickness of about 1.8 mm to 3.0 mm and a width of about 18 mm. The plates are configured to accept bone screws having a diameter of about 4.0 through 4.5 mm. Moreover, the bone screw holes of the plates are configured to accommodate both static and variable angle bone screws. This is accomplished by use of a unique pocket design of the bone screw holes. The bone screws are affixed using a typical screw driver (e.g. hexalobullar driver, ×10).

Once the plate has been installed with the appropriate bone screws, the bone screws may be locked via several methods. In one method, a single locking plate locks a pair of screws. The locking plate includes a center post that locks into a cover plate bore in the plate, and which has two configured flanges that are received in the head of the screw. In another form, the cover includes integral locking flanges for the bone screws. The cover and/or locking flanges are preferably made of PEEK, plastic, alloy or titanium.

A plate may be utilized as follows. A plate is placed onto the anterior aspect of a vertebral body of the cervical spine by inserting a 4.0 mm cancellous bone screw or a 4.3 mm expansion screw through the cephalad holes and into the vertebral body. The screw or expansion screws are then inserted into the caudal holes in the plate and inserted into the vertebral bodies of the cervical spine. The locking mechanisms are then inserted in a single step over the entire plate (e.g. a cover), or two locking mechanism are inserted over each set of screws (cephalad and caudel). The locking mechanisms will snap into place.

The present invention also provides for dynamically fusing the cervical spine of a patient via various methods, particularly, but not necessarily, utilizing a cervical plate as described herein. One such method includes the opening of an access aperture in the patient to permit access to an appropriate area of the cervical spine of the patient. A vertebral disc is removed between each vertebrae (level) as appropriate (e.g. one disc for a 1-L, two discs for a 2-L, etc.). Bone graft is then sized for placement into the space where the spinal disc has been removed. A dynamic cervical plate, such as any described herein, is selected for implanting onto the spine (vertabrae). The selected dynamic cervical plate is sized to allow for the best anatomical settling (motion), e.g. between 0 and 4 mm, of the vertebral bodies. The selected and sized dynamic plate is placed over the inserted bone graft(s) onto the vertebrae. The graft(s) is then visualized through the window(s) within the dynamic plate for proper fitment. Each section is accomplished in sequence for proper fitment. The plate is secured onto the spine by bone screws placed through the bone screw bores within the plate components or segments. After each bone screw is attached, a locking mechanism is installed onto/over the bone screws/plate. The aperture is then closed.

Another method of dynamically fusing the cervical spine includes providing a dynamic cervical plate wherein the end components of the provided dynamic cervical plate move relative to one another utilizing multiple projections (e.g. legs) sliding into or over one another according to the principles of the present invention. Another method of dynamically fusing the cervical spine includes providing a dynamic cervical plate wherein the end components of the provided dynamic cervical plate move relative to a middle segment/component utilizing multiple projections (e.g. legs) sliding into or over one another according to the principles of the present invention. Another method of dynamically fusing the cervical spine includes providing a dynamic cervical plate wherein the middle segments/components of the provided dynamic cervical plate move relative to one another utilizing multiple projections (e.g. legs) sliding into or over one another according to the principles of the present invention. Each plate providing a central graft window as provided herein for each level thereof.

Moreover, any of the methods, such as those immediately above, may include the providing of an n-level dynamic cervical plate, plate construct, or plate kit, wherein the end segments are 180° interchangeable, middle segments are 180° interchangeable, the end segments and the middle segments are 180° interchangeable, the end segments and the middle segments move 0 to 4 mm independent of the movement of one another, and/or the movement of the end segments and the middle segments is unconstrained.

The subject invention provides several key attributes that other plates and/or plate systems do not including:

1. The curvatures placed on the window portion of the plate allow the surgeon to align the plate more accurately to the vertebral body.

2. The curvatures placed on the window portion of the plate allow the surgeon to place bone screws more accurately because the bottom of the screw holes mate with a top of the plate window. This provides a positive visual indication that the plate is situated properly.

3. The screw holes have a unique geometry allowing a simple change of screws to utilize the plate as a variable angle screw/plate construct or as a fixed angle screw plate construct.

4. The plate construct may utilize an optional bone screw locking mechanism. The optional screw locking mechanism is a single-piece, snap on cover that is preferably, but not necessarily, made of PEEK or Titanium.

5. In one form, the optional screw locking mechanism attaches into the cervical plate by one of the midline holes. The locking mechanism will cover two screws at one time and lock into the plate using a pronged shaft. Radial projections (propeller like structures) have teeth on the extended ends that mate with the corresponding screws. The teeth lock into the lobes within the screw preventing them from both turning and backing out. This mechanism, like the other, snaps into place but remains removable with the proper instrument.

6. The dynamic plate form of the present invention will allow the fused vertebral bodies to settle onto the graft centered between them. This new dynamic plate and technique will allow fused segments to move, settle or subside which will provide for more constant bone-graft-bone contact. The present dynamic plate design allows the settling to occur in an anatomical fashion, due to plate curvatures. The bodies will translate in stabilized directions on two separate planes (pure translation).

7. The present invention provides the ability to control subsidence of the plate. This is important in order to prevent the plate from migrating into the healthy adjacent disc space. Moreover the present invention aids in preventing the destruction of the host endplate or the graft from unmitigated settling that may lead to pseudarthrosis. It should be appreciated that the above description is only exemplary of the principles of the subject invention. Therefore, other embodiments are contemplated and within the present scope.

While this invention has been described as having a preferred design, the present invention can be further modified within the spirit and scope of this disclosure. This application is therefore intended to cover any variations, uses, of adaptations of the invention using its general principles. Further, this application is intended to cover such departures from the present disclosure as come within known or customary practice in the art to which this invention pertains and that fall within the limits of the appended claims.

What is claimed is:

1. A bone screw retention device comprising:
a body having a plate, a center projection, and two outward prongs, the center projection and the two outward prongs being integral to the plate and extending from the plate in substantial parallel directions;
the center projection having at least one cervical plate engaging portion configured to seat into a center bore between a pair of bone screw bores in a cervical plate in a linear insertion and snap-fit or press-fit engagement; and the two outward prongs extending from the plate and adapted to engage respective bone screw drive sockets of a pair of bone screws seated in a cervical plate and create an interference with the bone screw drive sockets to retain and provide rotational prevention of the bone screws;

wherein the plate includes an upper surface and a lower surface, the plate being without a through-hole extending between the upper surface and the lower surface and without a recess in the upper surface.

2. The bone screw retention device of claim 1, wherein:
the two outward projections are adapted to engage lobes of the bone screw drive sockets of the seated bone screws in the cervical plate.

3. The bone screw retention device of claim 1, wherein the center projection is configured to be releasably seated into the center bore between the pair of bone screw bores in the cervical plate.

4. The bone screw bore of claim 3, wherein the at least one cervical plate engaging portion includes a diameter that is larger than a diameter of the center bore in the cervical plate.

5. The bone screw bore of claim 4, wherein the at least one cervical plate engaging portion is compressible to a diameter that is less than the diameter of the center bore in the cervical plate.

6. The bone screw retention device of claim 1, wherein the body is fashioned from one of a biocompatible titanium, titanium alloy, other metal alloy, PEEK, or another biocompatible material.

7. The bone screw retention device of claim 1, wherein the center projection and the two outward prongs are an integral, one piece component.

8. The bone screw retention device of claim 1, wherein the center projection includes at least one slot so that the cervical plate engaging portion compresses as it engages the opening on the cervical plate.

9. The bone screw retention device of claim 8, wherein the at least one slot extends parallel with a longitudinal axis of the center projection.

10. The bone screw retention device of claim 8, wherein the at least one slot comprises a plurality of slots.

11. The bone screw retention device of claim 1, wherein the center projection includes at least one notch so that the cervical plate engaging portion compresses as it engages the opening on the cervical plate.

12. The bone screw retention device of claim 11, wherein the at least one notch comprises a plurality of notches.

13. A bone screw retention device for use with a cervical plate and a pair of bone screws, the cervical plate having a top surface and a center bore located between a pair of bone screw bores, the bone screw retention device comprising:

a body formed of any one a biocompatible titanium, titanium alloy, other metal alloy, PEEK, or another biocompatible material;

the body defining a continuous plate having multiple projections configured to engage with respective center bore and pairs of bone screw bores in the cervical plate, the plate having an upper surface and a lower surface;

wherein the multiple projections are integrally formed with the plate and include a first projection, a second projection, and a third projection, the first projection having a rim and at least one slot configured to allow the rim to compress for a snap-fit or press-fit engagement with the cervical plate;

the continuous plate is includes an upper surface and a lower surface, the plate being without a through-hole extending between the upper surface and the lower surface and without a recess in the upper surface, and wherein the continuous plate is configured to engage the top surface of the cervical plate and at least a portion of each one of the bone screw bores of the cervical plate without being rotated into place.

14. The bone screw retention device of claim 13, wherein the at least one slot extends parallel with a longitudinal axis of the center projection.

15. The bone screw retention device of claim 13, wherein the at least one slot comprises a plurality of slots.

* * * * *